United States Patent
Byrne et al.

(10) Patent No.: US 6,797,729 B1
(45) Date of Patent: Sep. 28, 2004

(54) THERAPEUTIC GLUTAMINE AND N-ACTYL-CYSTEINE COMPOSITION

(75) Inventors: Theresa A. Byrne, Boston, MA (US); Joanne A. Somerville, Reading, MA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/884,170

(22) Filed: Jun. 27, 1997

(Under 37 CFR 1.47)

Related U.S. Application Data

(60) Provisional application No. 60/020,864, filed on Jun. 28, 1996.

(51) Int. Cl.[7] .................... A61K 31/195; A61K 31/015; A61K 31/34; A61K 31/35
(52) U.S. Cl. ....................... 514/562; 514/563; 514/763; 514/474; 514/455
(58) Field of Search ................................. 514/562, 563, 514/763, 474, 458

(56) References Cited

U.S. PATENT DOCUMENTS 5,491,150 A * 2/1996 Aoki et al. .................. 514/310

OTHER PUBLICATIONS

Sappey et al 121 CA 253510b, 1994.*
Al–Razzak et al 123 CA:314522x, 1995.*
Roederer et al 120 CA:289227h, 1994.*
Seh Rauzer et al 121 CA 49679j, 1994.*
Harakeh et al 121 CA 49680c, 1994.*
Wang et al Drugs, vol. 48 (3) pp 327–38, 1994.*
J.K. Shabert and D.W. Wilmore *Glutamine Deficiency as a Cause of Human Immunodeficiency Virus Wasting*, Brigham and Women's Hospital, Boston, MA, *Medical Hypothesis* (1996) 46,252–256, Pearson Professional Ltd. 1996.

* cited by examiner

*Primary Examiner*—Russell Travers
(74) *Attorney, Agent, or Firm*—Jeffrey C. Nichols; Mark J. Buonaiuto; Francis C. Kowalik

(57) ABSTRACT

Compositions comprising glutamine in combination with other ingredients such as N-acetyl-cysteine are disclosed. Such compositions can be administered to treat patients with certain conditions of the body.

13 Claims, No Drawings

THERAPEUTIC GLUTAMINE AND N-ACTYL-CYSTEINE COMPOSITION

This application claims benfit of No. 60/020,864 filed Jun. 28, 1996 now abandoned.

BACKGROUND OF THE INVENTION

1. Field of the Invention

The present invention relates to the use of the amino acid glutamine in combination with antioxidants or other precursors (such as N-acetyl-cysteine) as a nutritional supplement for patients with certain conditions of the body.

2. Discussion of the Background of the Invention

Malnutrition and the wasting of protein-containing muscle mass are major clinical consequences of infection with human immunodeficiency virus (HIV). Both contribute to the progression, morbidity and mortality of the disease. The etiology of the malnutrition and skeletal muscle wasting is multifactorial and includes: 1) hypermetabolism (or other metabolic derangements), 2) gastrointestinal dysfunction particularly impaired nutrient absorption and 3)inadequate food intake. Because there remains no definitive cure for HIV and resulting acquired immunodeficiency syndrome (AIDS), the medical and nutritional management of these patients has focused on the preservation of skeletal muscle mass, limiting symptoms (e.g., diarrhea, malabsorption) associated with gastrointestinal dysfunction, the prevention of opportunistic infections, and the enhancement of host immune defense.

Normal Metabolic Functions of Glutamine

Glutamine is a non-essential amino acid which can be synthesized by most tissues. Unlike most amino acids, glutamine has two amine moieties: an alpha-amino group and an amide group. It is the presence of the amide group which enables glutamine to remove ammonia from the peripheral tissues of the body and transport nitrogen to visceral organs. In addition, it is common for tissues that remove glutamine from the circulation to utilize the carbon skeleton for energy.

Glutaminase and glutamine synthetase are the two principal enzymes involved in the regulation of glutamine metabolism. Glutaminase catalyzes the hydrolysis of glutamine to glutamate and ammonia, while glutamine synthetase catalyzes the synthesis of glutamine from glutamate and ammonia. While most tissues have both of these enzymes, usually one is more active than the other, depending on the particular tissue.

Glutamine synthesis and exportation occurs primarily in skeletal muscle and the brain. In turn, glutamine is consumed by such replicating cells as fibroblasts, lymphocytes, tumor cells and intestinal epithelial cells. Characteristically, these cells possess high levels of glutaminase activity and low levels of intracellular glutamine. This fact may also be clinically significant for patients having large wounds, inflammation associated with infection, or a gastrointestinal dysfunction which precludes normal enteral feeding since, in these cell types, the desirable proliferation of cells in these conditions may depend on the availability of sufficient levels of glutamine. Glutamine is the most abundant free amino acid in the body and is involved with a dynamic inter-organ network—being released from the skeletal muscle (the major site of glutamine synthesis) to be utilized and metabolized throughout the body. Rapidly replicating cells (e.g. enterocytes, lymphocytes, macrophages) remove glutamine from the circulation and often utilize its 5 carbon chain for energy. Metabolism of glutamine to alpha-ketoglutarate and subsequent complete oxidation via the Krebs cycle yields 30 moles of ATP per mole of glutamine. Glutamine also plays a pivotal role in whole body nitrogen metabolism due to its two amine moieties, an alpha-amino group and an amide group, and acts as a "nitrogen shuttle" among various organs. Glutamine serves as a vehicle for transporting ammonia in a nontoxic form from the peripheral tissues to the kidney to be excreted as ammonium, or to the liver to be converted to urea. Glutamine also provides nitrogen for the synthesis of purines and pyrimidines and other amino acids, and thus—proteins. In addition, glutamine serves as a precursor to glutathione, a potent antioxidant important to limiting tissue damage from radical attack.

Alterations in Glutamine Metabolism

The stress associated with infection, prolonged illness or severe injury results in profound alterations in whole body and inter-organ glutamine metabolism. These hypermetabolic conditions (e.g., AIDS) are characterized by severe catabolism, wasting of protein-containing skeletal muscle mass, impairment in vital organ function and immunosuppression. The hormonal and inflammatory mediator milieu creates a generalized response in which amino acids are mobilized from the skeletal muscle in order to provide energy and substrate to support inflammation, immune response and tissue repair, and to assist in the maintenance of organ function.

Glutamine is a primary amino acid released from the skeletal muscle during stressed states. This accelerated release of glutamine from the periphery is matched with increased uptake by the intestinal tract, lymphoid tissue, liver and kidney. When the stress is prolonged, glutamine is consumed at rates faster than it can be synthesized and released from the skeletal muscle; the wasting of body nitrogen and skeletal muscle mass ensues. Glutamine levels in both the plasma and tissue pools diminish, creating a "deficiency" state. This lack of adequate glutamine alters the structure and/or function of those cells (e.g., enterocytes, lymphocytes, macrophages) dependent upon glutamine. Thus, under conditions of prolonged stress (e.g., HIV infection, AIDS, injury) glutamine has been classified as a "conditionally" essential amino acid. Glutamine supplementation restores amino acid concentrations in the plasma towards normal, limits the loss of protein-containing mass, and enhances tissue structure and/or function.

Glutamine Supplementation and the Preservation of Body Protein

In adult patients with AIDS, the timing of death is related to the degree of depletion of the body's protein-containing, metabolically active, functioning cellular mass. The body's cellular mass (BCM) constitutes approximately 30–38% of total body weight and approximately 55% of total body protein—with the majority present in the skeletal muscle mass and visceral organs. AIDS is associated with an accelerated loss of protein-containing tissue which is out of proportion to the loss of weight and fat mass. Even in asymptomatic HIV-infected adults, there can be a loss of this functional, protein-containing mass without significant changes in body weight or body mass index.

Stress (e.g. prolonged or repeated infections) induces an accelerated release of glutamine from the skeletal muscle protein, resulting in a decrease in intracellular muscle glutamine concentrations. Under such conditions, glutamine supplementation can minimize this decrease in muscle glutamine content. Clinically, this is important because a statistically significant correlation between survival in septic patients and intracellular muscle glutamine concentrations has been demonstrated.

In addition to decreased skeletal muscle glutamine concentrations, prolonged stress (such as that which is associated with HIV infection and AIDS) can result in severe wasting of skeletal muscle protein (nitrogen), which in turn suits in a precipitous fall in physiologic function. Clinically this manifests as skeletal muscle and respiratory muscle weakness, poor wound healing, and further impairment in immune function.

Glutamine supplementation has been shown to improve nitrogen (protein) balance in stressed and immunocompromised patients. Others have shown that glutamine supplementation can reduce myofibrillar protein breakdown and enhance skeletal muscle protein synthesis. These findings suggest that glutamine supplementation contributes to the preservation of the protein-containing tissue mass; and thus, may limit the physical debility and immunosuppression associated with its loss.

Glutamine Supplementation and the Preservation of Gut Structure and Function

Gastrointestinal tract dysfunctions are common complications of HIV infection. Anorexia, early satiety, nausea, abdominal pain, mouth or esophageal infections, gastrointestinal dysmotility, etc., can prevent adequate oral intake. In addition, infections of the gastrointestinal tract, either from opportunistic infections or HIV itself, can result in significant maldigestion, malabsorption, and severe diarrhea. Although these complications impair the primary role of the gastrointestinal tract (ingestion, digestion and absorption of nutrients), prolonged stress and the lack of luminal nutrients can compromise the barrier function of the intestinal epithelium to enteric flora or their toxins. This impairment in bowel integrity and increase in mucosal permeability is thought to result in the subsequent translocation of enteric bacteria and their endotoxins into the systemic circulation, initiating a septic process. Thus, under conditions of prolonged stress, the maintenance of a healthy gut appears to require a variety of therapeutic maneuvers, including the provision of glutamine.

Glutamine is the principle fuel source for the enterocytes and is necessary for the maintenance of intestinal metabolism, structure, and function, both in normal and in stressed states. In animals, the intentional lowering of blood glutamine levels via an infusion of glutaminase results in diarrhea, mild villous atrophy, mucosal ulcerations and intestinal necrosis. The addition of glutamine to standard amino acid solutions has been shown to prevent the villous atrophy associated with the provision of total parenteral nutrition (TPN) in the absence of enteral feedings. Others have shown that the improvement in gut mucosa integrity (associated with intravenous glutamine supplementation) inhibits the absorption of endotoxin across the bowel. In patients unable to take adequate enteral nutrition, the addition of glutamine to standard TPN solutions has been shown to prevent TPN-induced gut permeability.

More recently, investigators have explored the effects of enteral (rather than the parenteral) glutamine on bowel structure and function. In humans, approximately 50% of enterally administered glutamine is metabolized by the intestinal mucosa; the amount reaching the peripheral circulation is dependent upon the concentration delivered. The enteral administration of glutamine has been shown to prevent bowel permeability, decrease bacterial translocation, and improve survival in numerous models of gut-origin sepsis.

Others have described the trophic or reparative effects of enteral glutamine on the bowel mucosa. Klimberg et al. demonstrated that enterally administered glutamine supported crypt cell proliferation, accelerated small bowel healing and improved outcome following abdominal radiation (Klimberg et al., Cancer 1990;66:62–68). Jacobs et al., Surg Forum 1987;38:45–47, described the protective effects of glutamine on the colon in animals receiving chemotherapy. Studies have also shown that glutamine supplementation can accelerate bowel hyperplasia following extensive intestinal resection. (Gouttebel et al. JPEN 1992;16:117–121).

Glutamine also appears to play an important role in maximizing bowel function by influencing absorption. Gardemann et al. demonstrated that the luminal (or enteral) administration of glutamine enhances glucose absorption; however, this effect was not observed when glutamine was administered intravenously. Others have described the ability of enteral glutamine to enhance sodium (and thus, water) absorption in various models of experimentally-induced diarrhea. These effects have important clinical implications due to the prevalence of diarrhea and malabsorption in patients infected with HIV and AIDS.

Smith et al. (Reissue U.S. Pat. No. 35,233) relates to a method of treating catabolic dysfunction by administering a therapeutically effective amount of glutamine. This document suggests the administration of glutamine alone in response to catabolic activity following surgery, sepsis, burn injury, cancer chemotherapy, radiation therapy/injury, glucocorticoid therapy, or inadequate food intake.

Glutamine Supplementation and the Function of the Immune System

The immune system is of fundamental importance in preventing and limiting infection. Malnutrition (which accompanies HIV infection and AIDS) adversely affects the patients' ability to mount an acute phase response and impairs cellular immune function. Others have proposed that under conditions of prolonged stress (e.g., that which accompanies HIV infection and AIDS) where the demand for glutamine exceeds the supply, the decrease in plasma concentrations of this nutrient contributes to immunosuppression. Thus, a "deficiency" of glutamine is thought to influence the progression of disease and the prevalence of opportunistic infection.

The skeletal muscle feeds glutamine to the cells of the immune system, namely the lymphocytes and macrophages. Glutamine provides the primary energy source for these cells. It is thought to be essential for optimal proliferation (in response to an antigenic challenge such as a bacterial or viral infection) and function of lymphocytes, and for the normal (secretary and phagocytic) function of nonproliferating cells such as the macrophages.

Physiologic levels of glutamine appear to be needed for normal phagocytosis in vitro. Others have shown that excess glutamine added to tissue culture media can enhance the phagocytosis and cytotoxicity of macrophages isolated from the blood of healthy control subjects and stressed patients. (Patores et al. Nutrition 1994;10:385–391). Until recently, little information has been available concerning the fuel that polymorphonuclear cells utilize for their metabolic and bactericidal functions. However, recent data suggest that glutamine enhances the bactericidal function of neutrophils in normal and stressed states. In severely immunocompromised patients who had undergone bone marrow transplantation, glutamine supplementation has been shown to decrease the incidence of clinical infection and total and site-specific microbial colonization, significantly shorten hospital length of stay and reduce hospital costs in comparison to similar patients who did not receive exogenous supplementation. (Bakerville et al. Br J Exp Path 1980;61:132–138; MacBurney et al. J Am Diet Assoc 1994;94:1263–1266).

It is known that glutamine deficiency is one of the causes of human immunodeficiency virus wasting (Shabert et al., Medical Hypotheses, 46, 252–56 (1996)). Glutamine is essential to support many of the metabolic processes which are critically effected during HIV infection.

Glutamine and other amino acids have been given to patients with immune-compromised states, both alone and in combination with an immunopotentiator such as levitinan, OK-432, or sizofiran. (Aoki et al. (U.S. Pat. No. 5,491,150)). In the '150 patent, glutamine is shown as useful both for its effects on the patient's natural killer activity and for its improvement of the therapeutic effect of immunopotentiators.

The Role of Antioxidants and Their Precursors

Glutathione (GSH), the body's main intracellular defence against oxidative stress, is decreased in the plasma, lung epithelial-lining fluid, and T-lymphocytes of individuals infected with HIV. This deficiency is thought to potentiate HIV replication and accelerate the progression of the disease, whereas GSH replacement therapy is thought to be effective in extending the latency and delaying the development of opportunistic infections.

Glutathione is a tripeptide consisting of glutamate, cysteine, and glycine. Some investigators have suggested that glutathione replacement therapy, especially with N-actyl-cysteine, may reverse the plasma thiol deficiency associated with HIV infection by providing the rate limiting constituent necessary for adequate GSH production. Others have shown that extracellular glutamine is preferentially used over glutamate for the synthesis of GSH in several tissues and cell types; thus, under some circumstances the availability of glutamine may be rate limiting for the synthesis of GSH. Such data world suggest that the co-administration of glutamine and N-actyl-cysteine may optimize tissue GSH stores.

The provision of other antioxidants nutrients (such as selenium, Vitamins C and E, beta carotene) may offer additional protection against oxidative cellular injury. Selenium is a co-factor necessary for the normal functioning of the enzyme glutathione peroxidase; blood levels of this nutrient are known to be diminished during the early stages of HIV infections and in patients with AIDS. Vitamin C is a water-soluble compound that exerts a spectrum of antioxidant activities due to its ability to react with numerous aqueous free radicals and reactive oxygen species. Vitamin C appears to exert a post-translational inhibitory effect on HIV by causing impairment of enzymatic activity. Alpha-tocopherol (Vitamin E) is a lipid-soluble compound present in biologic membranes and lipoproteins; it is the most abundant-lipid-soluble antioxidant in humans. Vitamin E supplementation has been shown to increase humoral and cell-mediated immunity and decrease lipid peroxidation. Beta carotene is also a lipid-soluble compound, and acts as an effective quencher of singlet oxygen. Beta carotene supplementation to HIV positive individuals has been shown to increase CD4 cell counts. Thus, the provision of antioxidants (and their precursors N-actyl-cysteine and glutamine) maybe necessary to limit oxidative injury and the associated pathological sequelae in patients with HIV infection and AIDS.

In summary, current evidence suggests that during conditions of prolonged stress (e.g. chronic infection, HIV infection, AIDS, etc.), the provision of adequate glutamine is essential to preserving the skeletal muscle glutamine pool, improving nitrogen balance, augmenting protein synthesis, preserving the integrity of the intestinal mucosa, enhancing the absorptive capacity of the bowel, and optimizing the function of the immune system. The data suggest that glutamine supplementation offers the potential to limit the skeletal muscle wasting, reduce diarrhea and malabsorption, enhance immune host defense, and reduce the incidence of opportunistic infections associated with HIV infection and AIDS.

Despite the documented benefits of administering glutamine alone, however, there still remains a need for improved compositions which are able to increase metabolic processes, enhance host defense mechanisms, and help prevent oxidative injury in immunocompromised patients.

SUMMARY OF THE INVENTION

Accordingly, it is an object of the invention to provide compositions and methods of treatment for immunocompromised patients, which compositions and methods are able to increase metabolic processes, enhance host defense mechanisms, and help prevent oxidative injury in such patients.

In accordance with one aspect of the invention, there are provided supplemental therapeutic compositions comprising glutamine and at least about 0.6 g N-actyl-cysteine per 10 g glutamine. The supplemental therapeutic compositions may also further comprise at least about 4500 IU beta carotene per 10 g glutamine. The supplemental therapeutic compositions may further comprise at least about 200 mg Vitamin C per 10 g glutamine. The supplemental therapeutic composition may further comprise at least about 125 IU Vitamin E per 10 g glutamine. The supplemental therapeutic composition may further comprise at least about 70 mcg selenium per 10 g glutamine. The supplemental therapeutic compositions may further comprise maltodextrin or other carbohydrate source such as dextrose. The supplemental therapeutic compositions may further comprise a pharmaceutically acceptable carrier and other additives normally associated with pharmaceutical compositions.

In accordance with another aspect of the invention, there is provided a method of treating patients with certain conditions of the body for which treatment with glutamine is advantageous. The method comprises administering a therapeutically effective dose of the above-described compositions.

Another aspect of the invention provides a method of treating patients with certain conditions of the body for which treatment with glutamine is advantageous comprising administering a therapeutically effective dose of a composition of the present invention enterally.

Another aspect of the invention provides a composition of the invention in a form suitable for mixing with food or beverages for oral administration.

Yet another aspect of the invention provides a method of treating patients with conditions including HIV infection or AIDS, other immune disorders, trauma, and bowel disease or dysfunction, comprising administering a therapeutically effective dose of the composition of the present invention.

DESCRIPTION OF THE PREFERRED EMBODIMENTS

Ingredients

The inventors have devised a supplementary therapeutic composition for treating patients with certain conditions of the body for which treatment with glutamine is advantageous. One of the ingredients is glutamine. Glutamine is a non-essential amino acid which can be synthesized by most tissues. The stress associated with infection, prolonged illness or severe injury results in profound alterations in whole body and inter-organ glutamine metabolism. These hypermetabolic conditions (e.g., AIDS) are characterized by severe catabolism, wasting of protein-containing skeletal muscle mass, impairment in vital organ function and immunosuppression. The hormonal and inflammatory mediator milieu creates a generalized response in which amino acids are mobilized from the skeletal muscle in order to provide energy and substrate to support inflammation, immune response and tissue repair, and to assist in the maintenance of organ function.

Glutamine supplementation has been shown to improve nitrogen (protein) balance in stressed and immunocompromised patients. Glutamine supplementation can reduce myofibrillar protein breakdown and enhance skeletal muscle protein synthesis. Findings suggest that glutamine supplementation contributes to the preservation of the protein-containing tissue mass; and thus, may limit the physical debility and immunosuppression associated with its loss. (Ziegler et al. Ann Int Med 1992;116:821–828; Hammarqvist et al. Ann Surg 1990;212:637–644).

It has been discovered that patients can benefit from pharmacologic compositions comprising glutamine along with other beneficial elements, as described in the present invention. In this regard, another such ingredient in the compositions according to the present invention is N-actyl-cysteine. Cysteine, along with glutamate and glycine, is a component of glutathione (a tridpeptide). Glutathione (GSH), the body's main intracellular defence against oxidative stress, is decreased in the plasma, lung epithelial-lining fluid, and T lymphocytes of individuals infected with HIV. This deficiency is thought to potentiate HIV replication and accelerate the progression of the disease, whereas GSH replacement therapy is thought to be effective in extending the latency and delaying the development of opportunistic infections.

The provision of other antioxidants nutrients (such as selenium, Vitamins C and E, and beta carotene) in the compositions according to the present invention may provide additional protection against oxidative cellular injury. Selenium is a co-factor necessary for the normal functioning of the enzyme glutathione peroxidase; blood levels of this nutrient are known to be diminished during the early stages of HIV infections and in patients with AIDS. Vitamin C is a water-soluble compound that exerts a spectrum of antioxidant activities due to its ability to react with numerous aqueous free radicals and reactive oxygen species. Vitamin C appears to exert a post-translational inhibitory effect on HIV by causing impairment of enzymatic activity. Alpha-tocopherol (Vitamin E) is a lipid-soluble compound present in biologic membranes and lipoproteins; it is the most abundant lipid-soluble antioxidant in humans. Vitamin E supplementation has been shown to increase humoral and cell-mediated immunity and decrease lipid peroxidation. Beta carotene is also a lipid-soluble compound, and acts as an effective quencher of singlet oxygen. Beta carotene supplementation to HIV positive individuals has been shown to increase CD4 cell counts. Thus, the provision of antioxidants (and their precursors N-actyl-cysteine and glutamine) may be necessary to limit oxidative injury and the associated pathological sequelae in patients with HIV infection and AIDS.

Advantageous Embodiments

The compositions, in accordance with this invention, comprise glutamine and at least about 0.6 g N-actyl-cysteine (NAC) per 10 g glutamine. Acceptable ranges of NAC are preferably from about 0.6 to about 3 g NAC per 10 g glutamine, exemplary quantities, for example, are 10 g glutamine and 1.5 g N-actyl-cysteine.

Additionally, it is advantageous for the composition to further comprise per 10 g glutamine at least about 4500 IU beta carotene, at least about 200 mg Vitamin C, at least about 125 IU Vitamin E, and at least about 70 mcg selenium. Preferably, acceptable ranges include from about 4500 to about 10,000 IU beta carotene, from about 200 to about 1000 mg Vitamin C, from about 125 to about 500 IU Vitamin E, from about 70 to about 100 mcg selenium, although higher amounts can be used. Exemplary quantities per 10 g glutamine are 6500 IU beta carotene, 800 mg Vitamin C, 200 IU Vitamin E, and 70 mcg selenium. Of course, in practicing the present invention those skilled in the art should take care to avoid generally recognized potentially toxic levels of some of the elements of the composition, these include 1000 mcg/day selenium, 2000 mg/day Vitamin C, 1200 IU/day Vitamin E.

It is also advantageous for the composition to comprise a carbohydrate source such as maltodextrin or dextrose, preferably in amounts of at least about 5 grams per 10 g glutamine. Preferably, acceptable ranges generally include about 5 to about 10 grams of maltodextrin per 10 g glutamine, and an exemplary quantity is 6 grams. In one preferred embodiment, three types of maltodextrin are utilized in processing, i.e., about 50% maltodextrin-100, about 25% maltodextrin-50, and about 25% maltodextrin-500.

Functional analogues, derivatives, substitution products, isomers, or homologues of glutamine which retain their characteristics are contemplated as equivalents. Preferred are those analogues capable of donating an amine group and being metabolized in the Krebs cycle. Most preferred are compounds which possess the amino acid residue at one terminus of a carbon chain and an amine moiety at the other terminus of the carbon chain. Functional analogues, derivatives, substitution products, isomers, or homologues of other ingredients of the composition which retain their respected characteristics also are contemplated as equivalents.

Compositions according to this invention provide therapeutic effects which exceed the expected additive effect of the individual ingredients.

Methods of Dosing

The composition should be administered to patients, with dosages decided by a physician skilled in the art on a case by case basis. Patients may receive multiple doses of a composition according to this invention per day depending on the amount of glutamine and other ingredients in the composition, their particular condition, nutritional needs, and body size. Where the compositions contain about 10 g glutamine, on average patients preferably will receive 2 to 4 doses per day but doses can range from 1 dose per day to a much higher level as determined by the patient's physician or health care provider.

This composition is particularly advantageous for treating patients for whom glutamine has been shown to be an effective supplement, i.e., those with HIV infection, AIDS, other immune disorders, trauma (including burns, severe wounds, and surgery), and bowel disease or dysfunction (including Crohn's disease, ulcerative collitis, and irritable bowel disease).

Methods of Manufacture

The claimed composition can be made by methods known to those skilled in the art. The elements comprising the composition are prepared by standard methods of blending and mixing at temperatures and moisture contents which allow blending to take place. The elements comprising the composition are preferably utilized in a dispersable form.

In another embodiment, the claimed composition can be prepared using a standard wet process involving taking the product into a slurry, then processing it through heating it to high temperatures known to those skilled in the art then placing it into a separate chamber where it is blended and granulated.

The compositions can be prepared for both enteral and parenteral administration.

EXAMPLE 1

The compositions according to the present invention can be prepared by commercially available processes of blending and mixing as known to those skilled in the art (AMT Labs, Salt Lake City, Utah).

Methods of Administration

The term "enteral" is intended to indicate that portion of the alimentary canal between the mouth and the anus. The administration of the composition can be by enteral.

An example of how the enteral administration of the composition is accomplished is by using small-bore tubing placed via the nose into the gastric or duodenal regions, or through surgical implantation as in, for example, gastrostomy, or jejunostomy.

Regardless of which route of administration is utilized, the composition can be administered either singly or as a dietary supplement.

When used as a dietary supplement, the composition can be mixed with an existing enteral or diet prior to administration to the patient. It is also possible to administer the composition without mixing it directly with the other components of a diet as, for example, in enteral feeding wherein the composition is not directly added to the main bottle, but instead is added to a common reservoir using a "piggy-back" bottle.

According to the method of the invention, the composition may be administered by simply modifying existing dietary formulas to contain the proper concentration of the elements in the composition. Most preferably, the elements of the composition would remain in a dry form such as, for example, a sterile lyophilized powder which is aseptically hydrated at the time of administration and mixed at the proper concentration with the other components of the dietary composition. Alternatively, the composition could be premixed with the other components of a dry formula which is aseptically rehydrated at time of administration, or stored as a frozen concentrate which is thawed and mixed at the proper concentration at time of use.

The use of the composition by the method according to the invention is ideally suited for the preparation of additional compositions. These additional compositions may comprise the claimed composition alone or in combination with other chemicals. These other chemicals can be pharmaceutically accept able carriers, as well as other active substances of the diet as, for example, free amino acids, protein hydrolysates, or oils.

Containers containing the composition of the invention can be used to facilitate the administration of the composition according to the method of the invention. These containers are designed to contain, for example, a single or a daily dosage of the composition to be administered to the patient.

Containers adapted for enteral administration of the composition alone or in combination with other compounds are especially useful. Such containers could comprise a receptacle for the liquid composition, and a liquid conducive means capable of attachment to a feeding tube. The liquid conducive means could be any object capable of conveying the liquid composition in the receptacle to the feeding tube such as, for example, plastic tubing.

The above disclosure generally describes the present invention. A more complete understanding can be obtained by reference to the specific examples which are provided herein for purposes of illustration only and are not intended to be limiting unless otherwise specified.

What is claimed is:

1. A supplemental therapeutic composition for patients with hypermetabolic conditions of the body comprising glutamine and at least 0.6 g of N-acetyl-cysteine per 10 g of glutamine.

2. The supplemental therapeutic composition according to claim 1, wherein said composition further comprises at least about 4500 IU beta carotene per 10 g glutamine.

3. The supplemental therapeutic composition according to claim 1, wherein said composition further comprises at least about 200 mg Vitamin C per 10 g glutamine.

4. The supplemental therapeutic composition according to claim 1, wherein said composition further comprises at least about 125 IU Vitamin E per 10 g glutamine.

5. The supplemental therapeutic composition according to claim 1, wherein said composition further comprises at least about 70 mcg selenium per 10 g glutamine.

6. The supplemental therapeutic composition according to claim 1, wherein said composition further comprises at least 5 g of a carbohydrate source selected from the group consisting of maltodextrin and dextrose per 10 g glutamine.

7. The supplemental therapeutic composition according to claim 1, wherein said composition contains a pharmaceutically acceptable carrier selected from the group consisting of a diluent, an excipient, and a tableting additive.

8. The supplemental therapeutic composition according to claim 1, wherein said composition contains additive agents selected from the group consisting of a sweetener, a flavor, and a texture agent.

9. A composition according to claim 1, comprising 10 g glutamine.

10. A method of treating patients with hypermetabolic conditions of the body comprising administering a therapeutically effective dose of the composition of claim 1.

11. A method according to claim 10, wherein said composition is administered enterally.

12. A composition, according to claim 1, wherein said composition is suitable for mixing with food or beverages for oral administration.

13. A method according to claim 10, wherein said conditions for which treatment with glutamine is advantageous, said conditions being selected from the group consisting of HIV infection, AIDS, other immune disorders, trauma, and bowel disease or dysfunction.

* * * * *